US012733860B2

(12) United States Patent
Frimerman et al.

(10) Patent No.: US 12,733,860 B2
(45) Date of Patent: Sep. 15, 2026

(54) MULTI-STREAM BIOLOGICAL SIGNAL PROCESSING

(71) Applicant: AccuLine Ltd., Petah-Tikva (IL)

(72) Inventors: Aharon Frimerman, Tel Aviv (IL); Shai Revzen, Pittsfield, MI (US); Benjamin Shani, Ramat HaSharon (IL); Moshe Barel, Petah-Tikva (IL)

(73) Assignee: AccuLine Ltd., Petah-Tikva (IL)

( * ) Notice: Subject to any disclaimer, the term of this patent is extended or adjusted under 35 U.S.C. 154(b) by 0 days.

(21) Appl. No.: 19/175,116

(22) Filed: Apr. 10, 2025

(65) Prior Publication Data

US 2025/0235142 A1 Jul. 24, 2025

Related U.S. Application Data

(63) Continuation of application No. PCT/IL2024/050749, filed on Jul. 29, 2024.

(Continued)

(51) Int. Cl.

*A61B 5/318* (2021.01)
*A61B 5/00* (2006.01)

(Continued)

(52) U.S. Cl.

CPC ............ *A61B 5/318* (2021.01); *A61B 5/0205* (2013.01); *A61B 5/7267* (2013.01); *G16H 10/60* (2018.01); *A61B 5/0816* (2013.01)

(58) Field of Classification Search

CPC ..... A61B 5/318; A61B 5/0205; A61B 5/7267; A61B 5/0816; G16H 10/60

See application file for complete search history.

(56) References Cited

U.S. PATENT DOCUMENTS 7,386,340 B2 * 6/2008 Schlegel ................ A61B 5/366 600/517
8,233,971 B2 * 7/2012 Zhou ...................... A61B 5/349 600/509

(Continued)

FOREIGN PATENT DOCUMENTS

| | | | | |
|---|---|---|---|---|
| CA | 3093789 | A1 * | 3/2021 | ............. G16H 50/30 |
| WO | WO-9955228 | A1 * | 11/1999 | ........... A61B 5/7267 |
| WO | WO 2025/027596 | | 2/2025 | |

OTHER PUBLICATIONS

International Search Report and the Written Opinion Dated Nov. 26, 2024 From the International Searching Authority Re. Application No. PCT/IL2024/050749. (9 Pages).

(Continued)

*Primary Examiner* — Michael J Lau
(74) *Attorney, Agent, or Firm* — The Roy Gross Law Firm, LLC; Roy Gross

(57) ABSTRACT

There is provided a computer implemented method of diagnosing a heart condition, comprising: accessing a time-synchronized dataset including a plurality of ECG cycles captured by an ECG sensor over a plurality of cardiac cycles of a subject that are time-synchronized with a plurality of physiological signals captured by at least one physiological sensor over a plurality of physiological cycles of the subject, subtracting a baseline from the plurality of ECG cycles, computing spatiotemporal variability of a combination of at least a portion of the plurality of ECG cycles and the time-synchronized plurality of physiological signals, analyzing the spatiotemporal variability of the combination, and diagnosing the heart condition according to the analysis.

29 Claims, 3 Drawing Sheets

Related U.S. Application Data

Figure 1:
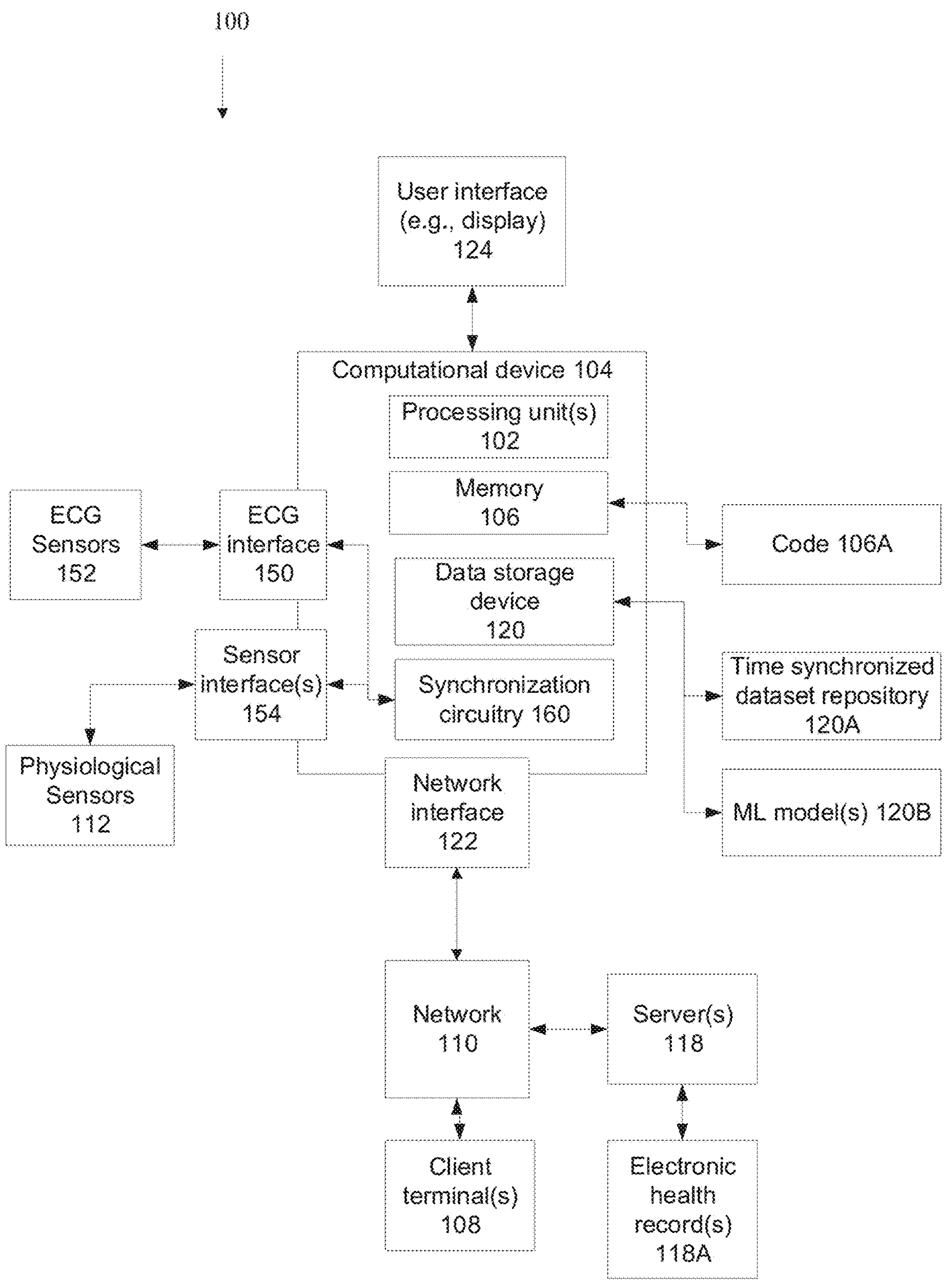

(60) Provisional application No. 63/530,080, filed on Aug. 1, 2023.

(51) Int. Cl.
*A61B 5/0205* (2006.01)
*G16H 10/60* (2018.01)
*A61B 5/08* (2006.01)

(56) References Cited

U.S. PATENT DOCUMENTS 8,934,964 B2 * 1/2015 Shani .................... A61B 5/349 600/509
9,014,795 B1 * 4/2015 Yang ........................ A61B 5/28 600/382
9,462,955 B2 * 10/2016 Zhou ....................... G16Z 99/00
10,517,487 B2 * 12/2019 Naghavi ............ A61B 5/02055
2003/0135097 A1 * 7/2003 Wiederhold ....... A61B 5/02405 600/509
2003/0176795 A1 * 9/2003 Harris .................. A61B 5/7285 600/485
2011/0066042 A1 * 3/2011 Pandia .................. A61B 5/029 600/513
2011/0190647 A1 * 8/2011 Helfenbein ........... A61B 5/721 600/509
2014/0207005 A1 7/2014 Bukkapatnam et al.
2015/0313484 A1 * 11/2015 Burg ...................... A61B 5/021 600/534
2017/0049352 A1 * 2/2017 Mirov .................. A61B 5/6843
2019/0307337 A1 * 10/2019 Little ................. A61B 5/02141
2020/0289000 A1 * 9/2020 Hall ..................... G01N 33/493
2021/0259765 A1 * 8/2021 Narayan ............ A61B 18/1492
2021/0272696 A1 * 9/2021 DeMazumder ........ G16H 15/00
2021/0391082 A1 * 12/2021 Amos ...................... G06N 3/09
2022/0095993 A1 * 3/2022 Karoly ................... G16H 50/30
2022/0117556 A1 4/2022 Kranck
2022/0296169 A1 * 9/2022 Alghorani .............. G16H 50/20
2022/0370017 A1 * 11/2022 DeMazumder ........ A61B 5/318
2023/0081751 A1 * 3/2023 Chatham ................ A61B 5/681 600/479
2023/0123838 A1 * 4/2023 Cohen .................... A61B 5/318 600/515
2023/0157647 A1 * 5/2023 Lambein ............ A61B 5/02416 600/479
2023/0172499 A1 * 6/2023 Marriott ............... A61B 5/7203 600/323
2023/0233121 A1 * 7/2023 Jooris .................... G16H 20/10 600/301

OTHER PUBLICATIONS

Frimerman et al. “Enhancement of Standard ECGs by a New Method for Multi-Cycle Superimposition and Summation”, The Israel Medical Association Journal, IMAJ, 20(1): 14-19, Jan. 2018.

* cited by examiner

MULTI-STREAM BIOLOGICAL SIGNAL PROCESSING

RELATED APPLICATIONS

This application is a Continuation of PCT Patent Application No. PCT/IL2024/050749 having International filing date of Jul. 29, 2024, which claims the benefit of priority under 35 USC § 119(e) of U.S. Provisional Patent Application No. 63/530,080 filed on Aug. 1, 2023. The contents of the above applications are all incorporated by reference as if fully set forth herein in their entirety.

BACKGROUND

The present invention, in some embodiments thereof, relates to analysis of sensor data and, more specifically, but not exclusively, to systems and methods for diagnosing a heart condition based on sensor data.

Heart conditions, in particular coronary artery disease (CAD) is diagnosed through a combination of medical history assessment, physical examination, and various diagnostic tests. Some common methods used for diagnosing CAD include:

1. Medical History and Physical Examination: The doctor will start by asking about medical history, risk factors, and any symptoms, such as chest pain (angina), shortness of breath, or fatigue. They will also perform a physical examination to check for signs of heart disease.
2. Electrocardiogram (ECG or EKG): An ECG is a non-invasive test that records the electrical activity of the heart. It can help detect abnormal heart rhythms (arrhythmias) and signs of previous or ongoing heart attacks.
3. Stress Tests: There are different types of stress tests, including exercise stress tests and pharmacological stress tests. During these tests, the heart's activity is monitored while the subject either exercises on a treadmill or receive medication that simulates the effects of exercise. Stress tests help evaluate how well the heart functions under stress and can indicate the presence of reduced blood flow to the heart muscle.
4. Coronary Angiography (Cardiac Catheterization): This invasive procedure involves threading a catheter through blood vessels to inject contrast dye into the coronary arteries. X-ray images are taken to visualize any blockages or narrowing in the coronary arteries. It is considered the gold standard for diagnosing CAD and determining the extent of the disease.
5. Echocardiogram (ECHO): An echocardiogram uses sound waves to create images of the heart. It helps assess the heart's pumping function, identify structural abnormalities, and evaluate blood flow through the heart's chambers.
6. Coronary Computed Tomography Angiography (CCTA): This non-invasive imaging technique uses computed tomography (CT) scans to visualize the coronary arteries and assess their condition.
7. Nuclear Imaging: Tests such as Single-Photon Emission Computed Tomography (SPECT) or Positron Emission Tomography (PET) can be used to evaluate blood flow to the heart muscle and identify areas with reduced blood supply.
8. Blood Tests: Blood tests, such as lipid profile, high-sensitivity C-reactive protein, and cardiac biomarkers (e.g., troponin), can provide information about cholesterol levels, inflammation, and possible heart muscle damage.

The specific diagnostic approach may vary depending on the individual patient's risk factors, symptoms, and overall health. Early diagnosis and intervention are crucial in managing coronary artery disease effectively.

SUMMARY

According to a first aspect, a computer implemented method of diagnosing a heart condition, comprises: accessing a time-synchronized dataset including a plurality of ECG cycles captured by an ECG sensor over a plurality of cardiac cycles of a subject that are time-synchronized with a plurality of physiological signals captured by at least one physiological sensor over a plurality of physiological cycles of the subject, subtracting a baseline from the plurality of ECG cycles, computing spatiotemporal variability of a combination of at least a portion of the plurality of ECG cycles and the time-synchronized plurality of physiological signals, analyzing the spatiotemporal variability of the combination, and diagnosing the heart condition according to the analysis.

According to a second aspect, a computer implemented method of training a machine learning model for diagnosis a heart condition of a subject, comprises: creating a multi-record training dataset for a plurality of individual, wherein a record comprises: at least one feature of spatiotemporal variability of a combination extracted from a time-synchronized dataset, and a ground truth indicating the heart condition of the individual, wherein the at least one feature is computed by: accessing the time-synchronized dataset including a plurality of ECG cycles captured by an ECG sensor over a plurality of cardiac cycles of the individual that are time-synchronized with a plurality of physiological signals captured by at least one physiological sensor over a plurality of physiological cycles of the individual, subtracting a baseline from the plurality of ECG cycles, computing the at least one feature as a spatiotemporal variability of a combination of at least a portion of the ECG cycles and the time-synchronized plurality of physiological signals, and training the ML model on the multi-record training dataset.

According to a third aspect, a device for diagnosing a heart condition of a subject, comprises: an ECG interface for connecting to at least one ECG sensor, at least one second interface for connecting to at least one physiological sensor, circuitry configured for generating a time-synchronized dataset including a plurality of ECG cycles captured by the ECG sensor over a plurality of cardiac cycles of the subject that are time-synchronized with a plurality of physiological signals captured by the at least one physiological sensor over a plurality of physiological cycles of the subject, and at least one processing executing a code for: subtracting a baseline from the plurality of ECG cycles, computing spatiotemporal variability of a combination of at least a portion of the plurality of ECG cycles and the time-synchronized plurality of physiological signals, analyzing the spatiotemporal variability of the combination, and diagnosing the heart condition according to the analysis.

In a further implementation form of the first, second, and third aspects, further comprising: for each ECG cycle of the plurality of ECG cycles, computing at least one correlation between at least one of: (i) the at least the portion of the ECG cycle and at least one corresponding individual physiological signal, (ii) the at least the portion of the ECG cycle and at least one other portion of the ECG cycle, (iii) the at least the portion of the respective individual ECG cycles and medical history of the subject, wherein computing the spatiotemporal variability of the combination comprises computing spatiotemporal variability of the at least one correlation over the plurality of ECG cycles.

In a further implementation form of the first, second, and third aspects, the correlation comprises a regression, and the spatiotemporal variability is expressed as the coefficients of the regression.

In a further implementation form of the first, second, and third aspects, further comprising computing an adapted baseline by adapting the baseline according to the correlation, wherein the spatiotemporal variability is computed for the plurality of ECG cycles relative to the adapted baseline.

In a further implementation form of the first, second, and third aspects, further comprising accessing medical records including the medical history of the subject, and wherein the spatiotemporal variability of the combination is analyzed with the medical history.

In a further implementation form of the first, second, and third aspects, further comprising extracting at least one feature of the spatiotemporal variability of the combination, wherein analyzing comprises feeding the at least one feature into a machine learning model, and wherein the diagnosis of the heart condition is obtained as an outcome of the machine learning model.

In a further implementation form of the first, second, and third aspects, the machine learning model is trained on a training dataset of a plurality of records for a plurality of individuals, wherein a record includes the at least one feature of spatiotemporal variability of the combination extracted from the time-synchronized dataset of an individual, and a ground truth indicating the heart condition of the individual.

In a further implementation form of the first, second, and third aspects, the spatiotemporal variability of the combination comprises variability of voltage of at least the portion of the plurality of ECG cycles.

In a further implementation form of the first, second, and third aspects, the spatiotemporal variability of the combination comprises variability of voltage of the plurality of ECG cycles as a function of the time-synchronized plurality of physiological signals.

In a further implementation form of the first, second, and third aspects, the plurality of physiological signals captured by at least one physiological sensor over a plurality of physiological cycles of the subject include a plurality of breathing signals captured by at least one respiration sensor over a plurality of respiratory cycles.

In a further implementation form of the first, second, and third aspects, the spatiotemporal variability of the combination comprises variability of voltage of the plurality of ECG cycles as a function of the plurality of respiratory cycles.

In a further implementation form of the first, second, and third aspects, the spatiotemporal variability of the combination comprises variability of voltage of at least a portion of the ECG cycles as a function of an inhalation phase and/or an exhalation phase.

In a further implementation form of the first, second, and third aspects, the plurality of breathing signals are captured by at least one respiration sensor comprising a tension sensor indicating changes in tension of a belt placed around a chest of the subject in response to expansion and contraction of the chest during inhalation and exhalation.

In a further implementation form of the first, second, and third aspects, the plurality of physiological signals captured by at least one physiological sensor over a plurality of physiological cycles of the subject include blood oxygenation signals captured by at least one blood oxygenation sensor over the plurality of cardiac cycles.

In a further implementation form of the first, second, and third aspects, the spatiotemporal variability of the combination comprises variability of voltage of at least a portion of the ECG cycles as a function of variability of blood oxygenation over the cardiac cycles.

In a further implementation form of the first, second, and third aspects, the plurality of physiological signals captured by at least one physiological sensor over a plurality of physiological cycles of the subject include blood volume signals denoting changes in blood volume captured by at least one blood volume sensor over the plurality of cardiac cycles.

In a further implementation form of the first, second, and third aspects, the spatiotemporal variability of the combination comprises variability of voltage of the plurality of ECG cycles as a function of variability of blood volume over the cardiac cycles.

In a further implementation form of the first, second, and third aspects, the at least the portion of the plurality of ECG cycles is selected from: between P and Q, between Q and R, between R and S, between S and T.

In a further implementation form of the first, second, and third aspects, further comprising: computing a delay between the physiological signals, and each one of a preceding corresponding ECG cycle, and time shifting the plurality of physiological signals to correspond to the plurality of ECG cycles, wherein the spatiotemporal variability is computed between the plurality of ECG cycles and the time shifted plurality of physiological signals.

In a further implementation form of the first, second, and third aspects, the spatiotemporal variability of the combination includes variability between successive ECG cycles.

In a further implementation form of the first, second, and third aspects, further comprising: classifying available signals into a plurality of classification categories, wherein computing the spatiotemporal variability of the combination comprises computing spatiotemporal variability within and/or across the plurality of classification categories.

In a further implementation form of the first, second, and third aspects, further comprising: classifying available signals into a plurality of classification categories, wherein computing the spatiotemporal variability of the combination comprises computing at least one correlation within and/or across the plurality of classification categories, wherein the spatiotemporal variability is of the at least one correlation.

In a further implementation form of the first, second, and third aspects, further comprising: classifying available signals into a plurality of classification categories, wherein computing the spatiotemporal variability of the combination comprises at least computing at least one coefficient of a regression between at least one first classification category and a target comprising at least one second classification category, wherein the spatiotemporal variability of the combination includes the at least one coefficient and/or is of the at least one coefficient.

In a further implementation form of the first, second, and third aspects, available signals include one or more of: (i) plurality of ECG signals, (ii) the baseline subtracted from the plurality of ECG signals, (iii) at least one of the time-synchronized plurality of physiological signals, (iv) delayed version of the plurality of physiological signals, (v) medical data of the subject.

In a further implementation form of the first, second, and third aspects, the plurality of classification categories include a first classification category indicating that a time interval of an ECG signal is above a median of time intervals of the plurality of ECG signals, and a second classification category indicating that the time interval of the ECG signal is below the median.

In a further implementation form of the first, second, and third aspects, the heart condition comprises coronary artery disease.

In a further implementation form of the first, second, and third aspects, further comprising treating the coronary artery disease of the subject by administering a treatment effective for coronary artery disease.

In a further implementation form of the first, second, and third aspects, further comprising: computing at least one coefficient of a regression between the plurality of physiological signal and a target comprising an ECG cycle of the plurality of ECG cycles corresponding to a physiological signal of the plurality of physiological signals, wherein the spatiotemporal variability of the combination includes the at least one coefficient.

In a further implementation form of the first, second, and third aspects, further comprising: computing a correlation between the plurality of ECG cycles and the plurality of physiological signals, computing an initial baseline according to a common portion of the plurality of ECG cycles of a raw ECG signal, adapting the initial baseline according to the correlation to compute an adapted baseline, adjusting the raw ECG signal according to the adapted baseline to obtain a corrected ECG signal, wherein the spatiotemporal variability is computed for the correct ECG signal.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 2:
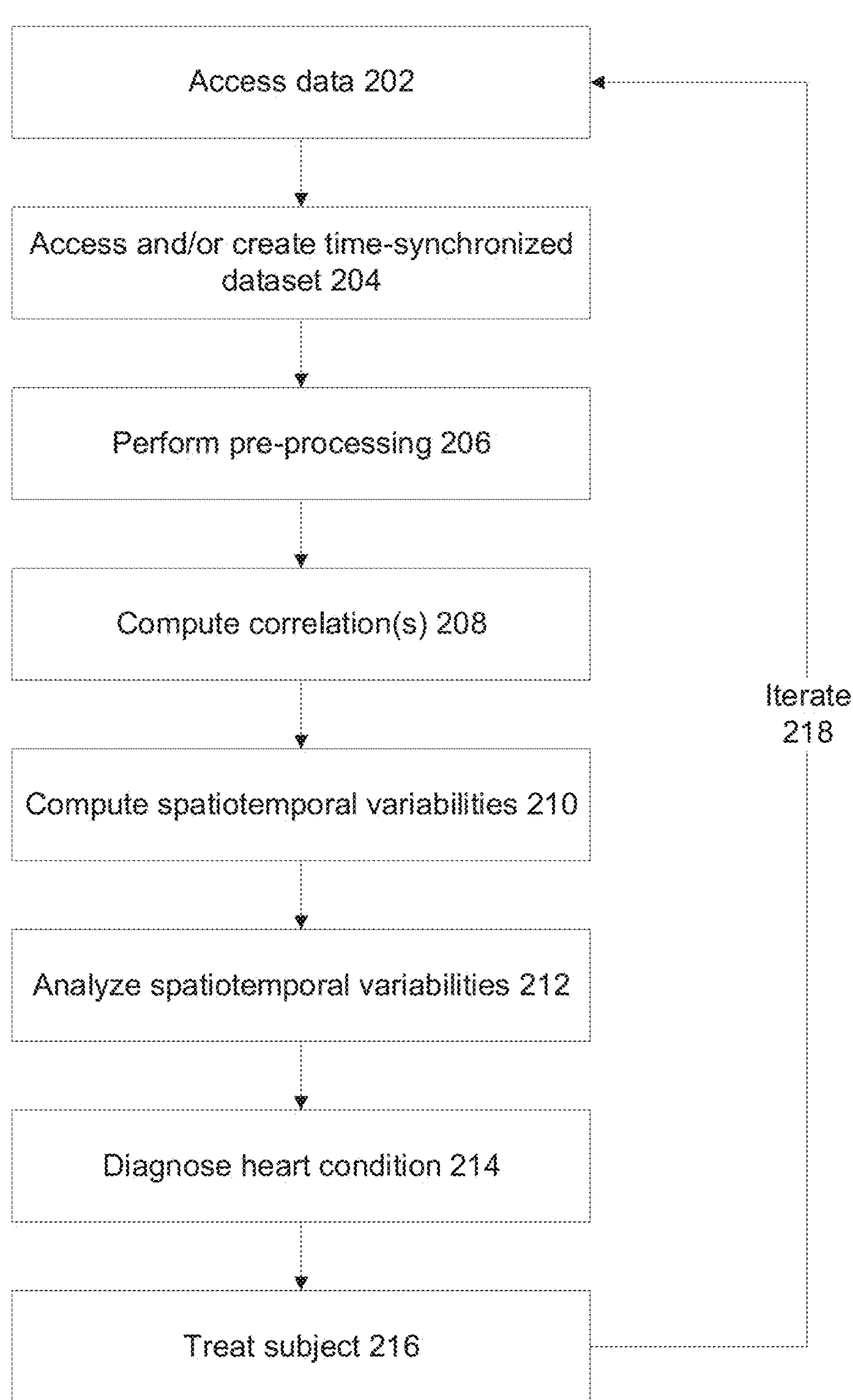
Figure 3:
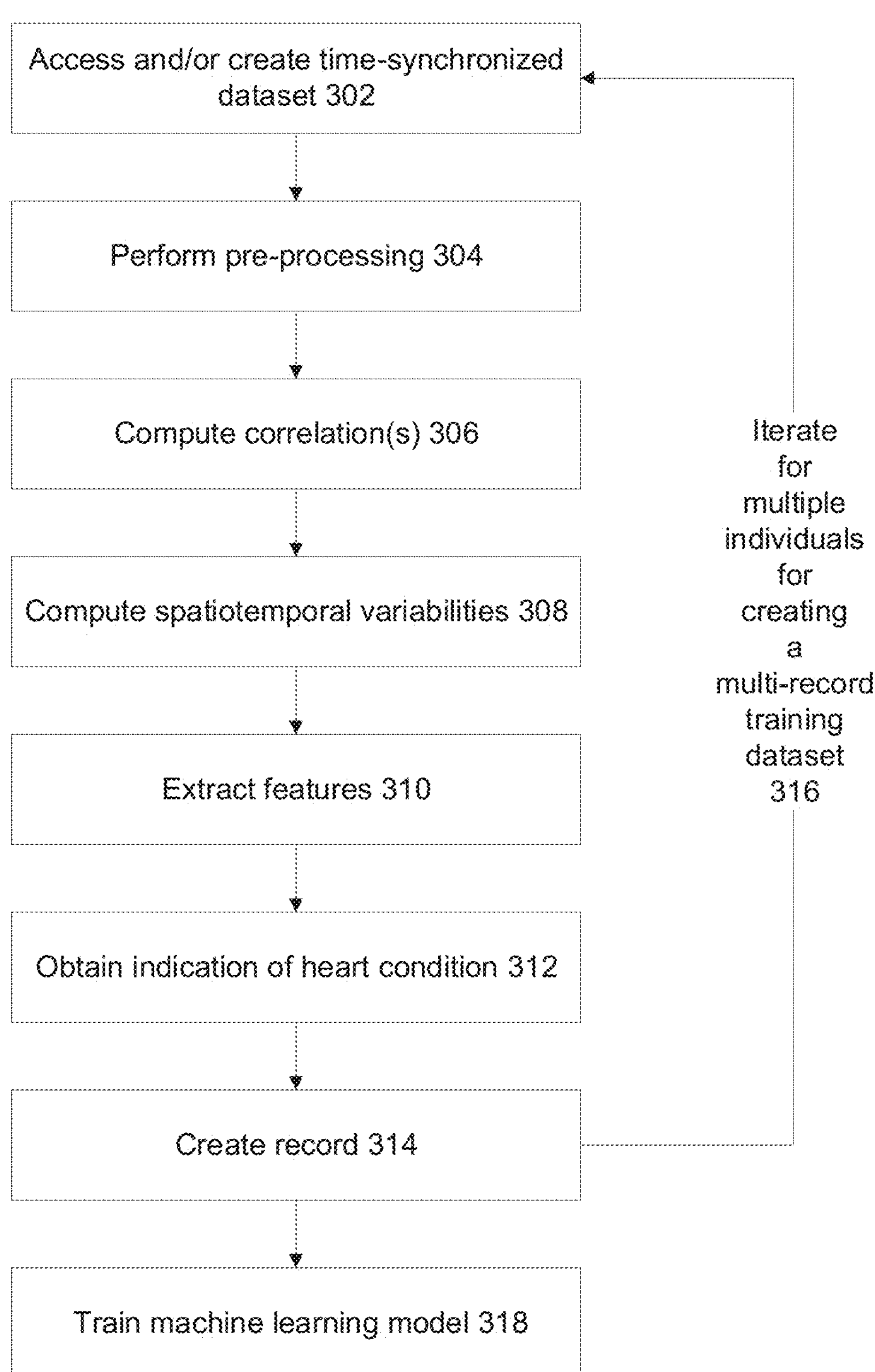

In the drawings:

FIG. 1 is a block diagram of components of a system for analyzing spatiotemporal variability of a time synchronized dataset of ECG and physiological measurements for diagnosing a heart condition, in accordance with some embodiments of the present invention;

FIG. 2 is a flowchart of a method of analyzing spatiotemporal variability of a time synchronized dataset of ECG and physiological measurements for diagnosing a heart condition, in accordance with some embodiments of the present invention; and FIG. 3 is a method of training a machine learning model for analyzing spatiotemporal variability of a time synchronized dataset of ECG and physiological measurements for diagnosing a heart condition, in accordance with some embodiments of the present invention.

DETAILED DESCRIPTION

The present invention, in some embodiments thereof, relates to analysis of sensor data and, more specifically, but not exclusively, to systems and methods for diagnosing a heart condition based on sensor data.

An aspect of some embodiments of the present invention relates to systems, methods, computing devices, and/or code (e.g., stored on a data storage device and executable by one or more processors) for diagnosing a heart condition, for example, coronary artery disease. A processor accesses a time-synchronized dataset that includes ECG cycles captured by an ECG sensor over multiple of cardiac cycles of a subject. The ECG cycles are time-synchronized with physiological signals captured by one or more physiological sensors over multiple physiological cycles of the subject. A baseline may be subtracted from the ECG cycles. Spatiotemporal variability of a combination of at least a portion of the ECG cycles and the time-synchronized physiological signals is computed. The spatiotemporal variability of the combination is analyzed, for example, by feeding into a trained machine learning model and/or in view of spatiotemporal variability of other subjects without the heart condition and/or with the heart condition. The heart condition may be diagnosed according to the analysis.

The spatiotemporal variability of the combination may relate to how values of the combination vary, for example, over time and/or space. The values of the combination may vary between ECG cycles in view of dynamics of the physiological cycles. The ECG cycles and the physiological signals are collected over time, at different spatial locations of the body. The spatiotemporal variability of the combination as described herein, is different than prior approaches, for example, standard approaches that check for ST segment depression, and/or that analyze changes in voltage of the ECG over time and/or between heart beats. The spatiotemporal variability of the combination as described herein, further considers other physiological cycles in combination with heartbeats, for example, for individuals with normal responses (e.g., without impact of a heart condition and/or neurological condition on nerve conduction), the rate of the beating heart changes as a function of the respiratory phase (e.g., inhalation and exhalation), i.e., increasing heart rate during the inhalation, and decreasing heart rate during the exhalation phase. Lack of expected response in changes of the rate of the beating heart with respect to the respiratory phase may indicate the heart condition, for example, damage to the heart which may trigger an arrhythmia. For example, when the rate of heartbeats do not slow down and/or speed up as expected for a healthy individual, a likelihood of the heart condition may be determined. Spatiotemporal variability of the combination that is based the ECG in view of the respiratory phase may provide a more accurate indication of the heart condition, in comparison to detecting abnormal response of the heart rate to the inspiration and/or expiration phase alone. For example, a certain portion of the ECG cycle's voltage response to the inspiration and/or expiration phase may be impacted, indicating the heart condition. Such change in response may be detected using some embodiments described herein.

In another example, for subjects with normal responses (e.g., without impact of a heart condition and/or neurological condition on nerve conduction), blood oxygenation may vary as a function of heartbeats. The heart pumping blood into the lungs increases the oxygenation level of the blood, which is then pumped into the rest of the body. A decrease in the oxygenation level of the blood (e.g., partial pressure of oxygen in the blood, such as measured by a pulse oximeter) as a function of the cardiac cycle (e.g., a portion of the ECG cycle) may indicate the heart condition. For example, ischemia in the heart tissue reduces the heart's ability to properly pump blood, causing a reduction in blood oxygenation. In another example, a failing heart that cannot properly pump blood may cause congestion in blood vessels towards the lung, which may result in a decrease in oxygen saturation in the arterial blood tree, which leads to a flow of insufficiently oxygenated blood to the heart itself. This creates a negative feedback cycle that further worsens the heart's function.

In yet another example, for subjects with normal responses (e.g., without impact of a heart condition and/or neurological condition on nerve conduction), blood volume may vary as a function of heartbeats. The contracting normal heart pushes blood into the vasculature, which results in increased blood volume, especially when the vasculature is healthy and/or elastic. During relaxation, the blood volume may decrease as the blood flows down the vasculature tree, especially when the vasculature is healthy and/or elastic. A change in the dynamics of blood volume as a function of the cardiac cycle (e.g., a portion of the ECG cycle), which may be caused by abnormalities of the beating heart and/or decreased elasticity of the arterial tree, may indicate the heart condition.

The spatiotemporal variability may be computed for a combination that includes one or more portions of the ECG cycle, rather than the ECG cycle as a whole, since each portion of the ECG cycle represents a different part of the heart and/or different functionality of the heart that may be impacted without necessarily impacting other parts and/or functions of the heart. For example, contraction of the atria, signals passing through the bundle of His, signals being conducted and distributed across a network to different parts of the ventricles, contraction of the ventricles, and the like. Examples of at least the portion of the ECG cycle of the combination for which spatiotemporal variability is computed include one or more of: between P and Q, between Q and R, between R and S, between S and T.

An aspect of some embodiments of the present invention relates to systems, methods, computing devices, and/or code for training a machine learning model for diagnosis a heart condition of a subject. A multi-record training dataset is created using data from multiple individuals. A record includes at least one feature of spatiotemporal variability of a combination extracted from a time-synchronized dataset, and a ground truth indicating the heart condition of the individual. The feature(s) is computed by accessing the time-synchronized dataset, that includes ECG cycles captured by an ECG sensor over cardiac cycles of the individual. The ECG cycles are time-synchronized with physiological signals captured by the physiological sensor(s) over physiological cycles of the individual. A baseline may be subtracted from the ECG cycles. The feature(s) is computed as a spatiotemporal variability of a combination of at least a portion of the ECG cycles and the time-synchronized physiological signals.

An aspect of some embodiments of the present invention relates to systems and/or devices for diagnosing a heart condition of a subject. The system and/or device includes an ECG interface for connecting to an ECG sensor, at least one second interface for connecting to at least one physiological sensor, and circuitry configured for generating a time-synchronized dataset including ECG cycles captured by the ECG sensor over cardiac cycles of the subject that are time-synchronized with physiological signals captured by the physiological sensor(s) over physiological cycles of the subject. The system and/or devices may include a processor (s) executing a code for: optionally subtracting a baseline from the plurality of ECG cycles, computing spatiotemporal variability of a combination of at least a portion of the ECG cycles and the time-synchronized physiological signals, analyzing the spatiotemporal variability of the combination, and diagnosing the heart condition according to the analysis.

At least some embodiments described herein address the technical problem of providing a simple, non-invasive approach (e.g., device) for diagnosing a heart condition, for example, coronary artery disease. At least some embodiments described herein improve the technology of signal processing and/or machine learning, by providing a simple, non-invasive approach for diagnosing a heart condition. At least some embodiments described herein improve upon prior non-invasive approaches of diagnosing a heart condition. Standard approaches are based on analyzing an ECG, obtained using standard approaches. Such standard ECGs have relatively low diagnostic accuracy.

At least some embodiments described herein provide solutions to the aforementioned technical problem, and/or improve the aforementioned technical field, and/or improve upon the aforementioned standard approaches, by analyzing spatiotemporal variability of a combination of at least a portion of ECG cycles that are time-synchronized with physiological signals, for diagnosing the heart condition.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference is now made to FIG. 1, which is a block diagram of components of a system 100 for analyzing spatiotemporal variability of a time synchronized dataset of ECG and physiological measurements for diagnosing a heart condition, in accordance with some embodiments of the present invention. Reference is also made to FIG. 2, which is a flowchart of a method of analyzing spatiotemporal variability of a time synchronized dataset of ECG and physiological measurements for diagnosing a heart condition, in accordance with some embodiments of the present invention. Reference is also made to FIG. 3, which is a method of training a machine learning model for analyzing spatiotemporal variability of a time synchronized dataset of ECG and physiological measurements for diagnosing a heart condition, in accordance with some embodiments of the present invention.

System 100 may implement the features of the method described with reference to FIGS. 2-3, by one or more hardware processors 102 of a computing device 104 executing code instructions stored in a memory (also referred to as a program store) 106.

Computing device 104 may be implemented as, for example, a standalone device, a component that may be connected to an existing device, a client terminal, a server, a virtual machine, a virtual server, a computing cloud, a mobile device, a desktop computer, a thin client, a Smartphone, a Tablet computer, a laptop computer, a wearable computer, glasses computer, and a watch computer.

Computing device 104 may include an ECG interface 150 for connecting to one or more ECG sensors 152. ECG cycles captured by ECG sensors 152 may be different than standard ECG signals captured by a standard ECG sensor, for example, having a higher sampling rate to enable detecting spatiotemporal variability.

Computing device 104 may include one or more sensor interfaces for connecting to one or more physiological sensors 112. Examples of physiological sensors 112 include: a belt for placing around a chest for sensing expansion and contraction of the chest during inhalation and exhalation, and a pulse oximeter that senses oxygen levels in blood (SpO2) and/or blood volume changes.

Computing device 104 may include synchronization circuitry 160 that receives the ECG measurements by ECG sensors 152 (e.g., via ECG interface 150) and physiological measurements by physiological sensors 112 (e.g., via sensor interface(s) 154), and generates the time-synchronized dataset described herein.

In some architectures, synchronizations circuitry 160, ECG interface 150, and sensor interface(s) 154 are arrange in a separate device (e.g., external device with its own housing) which is connected to computing device 104, for example, directly and/or via a network.

Multiple architectures of system 100 based on computing device 104 may be implemented. In an exemplary implementation, computing device 104 storing code 106A may be implemented as one or more servers (e.g., network server, web server, a computing cloud, a virtual server) that provides services (e.g., one or more of the acts described with reference to FIGS. 2-3) to one or more servers 118 and/or client terminals 108 over a network 110, for example, providing software as a service (SaaS) to the servers 118 and/or client terminal(s) 108, providing software services accessible using a software interface (e.g., application programming interface (API), software development kit (SDK)), providing an application for local download to the servers 118 and/or client terminal(s) 108, and/or providing functions using a remote access session to the servers 118 and/or client terminal(s) 108, such as through a web browser and/or viewing application. For example, users use client terminals 108 to access computing device 104 to provide the time-synchronized datasets generated by a local synchronization circuitry, and/or to provide the ECG measurements and/or physiological sensor measurements acquired by the ECG sensors and physiological sensors, and/or view and/or receive the diagnosis of the heart condition. For example, using an installed application and/or by using a web browser to connect to computing device 104, and/or communicating data with computing device 104 using a software interface (application programming interface (API) and/or software development kit (SDK). In another example, computing device 104 is a standalone system, for example, a standalone device which may be connected to ECG sensors 152 and/or physiological sensors 112 and running locally stored code 106A for locally diagnosing subjects.

Sensor(s) 152 and/or sensor(s) 112 may transmit data to ECG interface 150 and/or sensor interface(s) 154 of computing device 104, for example, via a direct connected (e.g., local bus and/or cable connection and/or short range wireless connection), and/or via a network 110 and a network interface implementation of ECG interface 150 and/or sensor interface(s) 154 computing device 104 (e.g., where sensors are connected via internet of things (IoT) technology and/or are located remotely from the computing device).

Network interface 122 and/or ECG interface 150 and/or sensor interface(s) 154 may be implemented as, for example, a wire connection (e.g., physical port), a wireless connection (e.g., antenna), a network interface card, a wireless interface to connect to a wireless network, a physical interface for connecting to a cable for network connectivity, and/or virtual interfaces (e.g., software interface, API, SDK, virtual network connection, a virtual interface implemented in software, network communication software providing higher layers of network connectivity).

Memory 106 stores code instructions executable by hardware processor(s) 102. Exemplary memories 106 include a random access memory (RAM), read-only memory (ROM), a storage device, non-volatile memory, magnetic media, semiconductor memory devices, hard drive, removable storage, and optical media (e.g., DVD, CD-ROM). For example, memory 106 may code 106A that execute one or more acts of the method described with reference to FIGS. 2-3.

Computing device 104 may include data storage device 120 for storing data, for example, time-synchronized dataset repository 120A that stores time-synchronized datasets generated by synchronization circuitry 160, ML model(s) 120B, and other data described herein. Data storage device 120 may be implemented as, for example, a memory, a local hard-drive, a removable storage unit, an optical disk, a storage device, a virtual memory and/or as a remote server 118 and/or computing cloud (e.g., accessed over network 110).

Computing device 104 includes and/or is in communication with one or more physical user interfaces 124 that include a mechanism for entering data and/or viewing data, for example, a touchscreen display used to indicate a new person for analysis, and/or for presenting the computed diagnosis of the heart condition. Exemplary user interfaces 124 include, for example, one or more of, a touchscreen, a display, a keyboard, a mouse, and voice activated software using speakers and microphone.

Computing device 104 may communicate with one or more servers 118 via network 110. For example, server(s) 118 store electronic health records(s) 118A of subjects, which may be accessed to obtain health data of a subject used for diagnosing the subject.

Referring now back to FIG. 2,

At 202, data may be accessed. The data may include cyclical measurements made by sensors.

Optionally, ECG cycles captured by one or more ECG sensors (e.g., electrodes) over multiple cardiac cycles of a subject are accessed. ECG cycles may be captured by one or more ECG sensors, which may be placed at standard locations for obtaining a standard ECG, and/or at other locations on the body not used for standard ECG readings. The ECG cycles may be sampled at a higher rate than that of standard ECG signals, to provide sufficiently high resolution for computing spatiotemporal variability. The ECG sensors may be attached to one or more standard locations on the body of the subject (e.g., for obtaining standard ECG readings) and/or to the V4 location. The ECG sensors and/or ECG sensing circuitry described herein may be different than standard ECG electrodes and/or standard ECG circuitry, for example, providing high sampling rates to enable computation of spatiotemporal variability, for example, at least about 1000 Hertz (Hz), or 1200 Hz, or 1500 Hz, or other values.

Optionally, medical record(s) that include the medical history of the subject are accessed. Examples of parameters of the medical history which may be obtained include: signs, symptoms, past medical history, previous surgeries, smoking history, family history, administered medications, and comorbidities.

Optionally, physiological measurements obtained by one or more physiological sensors are accessed. The physiological measurements may be obtained over multiple physiological cycles. Examples of physiological measurements and physiological sensors include:

Breathing signals captured by a respiration sensor over a respiratory cycles. For example, the respiration sensor may be implemented as a tension sensor indicating changes in tension of a belt placed around a chest of the subject in response to expansion and contraction of the chest during inhalation and exhalation.

Blood oxygenation signals (e.g., SpO2) captured by a blood oxygenation sensor over cardiac cycles, for example, a pulse oximeter, which may be placed on a finger of the subject.

Blood volume signals denoting changes in blood volume captured by a blood volume sensor over cardiac cycles. For example, using a pulse oximeter placed on a finger of the subject.

At 204, a time-synchronized dataset of the ECG cycles that are time-synchronized with physiological signals is created and/or accessed.

At 206, one or more pre-processing features may be performed. The pre-processing may be done on the time-synchronized dataset. Alternatively or additionally, the pre-processing is done on the data prior to generating the time-synchronized dataset.

To detect R wave peaks in the ECG cycle, a series of steps may be are followed. For example, first, the ECG leads are aggressively bandpass filtered above 60 Hz. Then, the sum of squares of these filtered leads may be computed to obtain an electrical power measurement. This power measurement may be thresholded to identify the areas around R wave peaks. To precisely locate the peaks with sub-sample accuracy, a quadratic fit may be applied to each identified area. Next, the median R-R interval may be computed and labeled, for example, as "rr". An index of "fast" beats may be created, which includes R-R intervals shorter than rr. The "fast" beats may be a classification category as described herein.

P and T waves may be identified. For example, a table of beats centered on the R wave and extending from −rr to +rr around may be is constructed. The sample median may be calculated at each offset in this table, resulting in a "median beat." By using a combination of filters with different window sizes, indicators for waves away from the electrical baseline may be found. These indicators may be further "debounced", for example, using a windowed median filter. To specifically identify the P and T waves, the following exemplary process may be used: (a) The wave containing the R peak may be designated as the R wave; (b) The largest wave before the R wave may be identified and labeled as P wave; (c) The largest wave after the R wave may be identified and labeled as T wave.

A non-linear filtered baseline, denoted bl[k], may be created for each ECG sensor denoted k. This may be done, for example, by interpolating lines in the T-P interval and connecting those lines using cubic splines in the P-T interval.

Approach described herein may ensures the accurate detection of R wave peaks and the identification of P and T waves in the ECG signal, which may be used for computing spatiotemporal variability of at least a portion of the ECG signal, as described herein.

Optionally, a baseline is subtracted from the ECG cycles. The baseline may be the bl[k] baseline described above. The baseline may be subtracted from ECG signals from raw ECG signals from each respective ECG sensor (denoted k), to obtain filtered ECG signals.

Alternatively or additionally, the baseline may be a T-P interval on the ECG, which may be considered as a "true zero" since there are no specific disease conditions that are known to elevate or depress the T-P segment.

The subtraction of the baseline may align the ECG cycles to a common reference, for enabling determination of variability between the ECG cycles and/or of the combination.

The beat table may be rebuilt from the filtered ECG signals.

Optionally, the physiological signals are time shifted relative to the ECG signals, optionally relative to the time-synchronized ECG signals. A delay may be computed between the physiological signals, and each one of a preceding corresponding ECG cycle. The physiological signals may be time shifted to correspond to the ECG cycles to account for the delay. Optionally, the physiological signals measured peripherally, such as at the limbs such as at the fingers, for example, blood volume changes, are time shifted relative to the ECG signals. For example, the delay between vein dilation in the SpO2 signal (i.e., physiological signal) and a previous R wave of the ECG signal may be computed. The SpO2 signal (e.g., time series) may be time shifted using the computed delay to correspond to the ECG cycle time base.

Time shifting may be done since physiological signals measured in peripheral locations relative to the heart (e.g., limbs) correspond to ECG signals at a different time. The difference is due to the time delay for physiological effect to propagates from the heart through the body. For example, the heart contracts and ECG cycles are record. However, veins in the finger do not expand instantly in synch with the heart contracting, since it takes time for the pressure wave of the blood to travels down the arterial tree. The time shifting is done to link the ECG cycle with the resulting physiological measurement while taking the delay into account. Moreover, in reconstructing the state of a dynamical systems, such as the cardiovascular system, delayed states may be used. Delayed states may be sufficient to reconstruct latent variables, for example, to anticipate the motion of a falling object it is insufficient to just measure its position. However, if the position of the object at two times separated by a known interval is available, the velocity may be computed (e.g., implicitly) and the future motion may be anticipated very accurately.

Optionally, the time-synchronized dataset is transformed, for creating a transformed time-synchronized dataset. For example, the time-synchronized dataset may be re-parameterized, and/or phase correction may be applied, such as to define the a phase of the physiological cycle(s) (e.g., inspiration, expiration, Sp02 phase) for computing the ECG cycle as a function of the physiological phase.

At 208, one or more correlations may be computed.

Correlations can be computed, for example as a regression, between at least a portion of an ECG cycle (e.g., one or more of pqrst waves), and one or more of the following: at least one corresponding individual physiological signal (e.g., breathing cycle, SpO2 signal optionally time shifted), at least one other portion of the ECG cycle (e.g., last RR interval, other wave), and medical history of the subject.

The regression (e.g., regressions described herein) may be implemented as, for example, a Fourier regression, and/or a linear regression.

Optionally, an adapted baseline is computed by adapting the baseline according to the correlation.

Alternatively or additionally, an initial baseline is computed according to a common portion of the ECG cycles of a raw ECG signal. The initial baseline may be adapted according to the correlation to compute an adapted baseline. The raw ECG signal may be adapted according to the adapted baseline to obtain a corrected ECG signal. The corrected ECG signal may be used in place of the ECG cycles descried herein.

At 210, one or more spatiotemporal variabilities are computed for a combination of at least a portion of the ECG cycles and the corresponding time-synchronized physiological signals. The physiological signals may include the time shifted physiological signals descried herein. The ECG cycles may include the correct ECG signal described herein.

The spatiotemporal variability may be computed between heart beats and/or between physiological cycles, i.e., inter-variability. The inter-variability is different than intra-variability, i.e., looking at changes within the ECG signals itself.

The spatiotemporal variability may be computed by optionally aligning the elements of the combination (e.g., at least the portion of the ECG cycle and corresponding time-synchronized physiological signals), “stacking” such as overlaying the elements (e.g., aligned elements) over each other, and analyzing the “spread” of the elements, such as mean, average, standard distribution, maximum value, minimum value, and the like.

Alternatively or additionally, the spatiotemporal variability may be computed for the transformed time-synchronized dataset, described with reference to 208 of FIG. 2.

Alternatively or additionally, the spatiotemporal variability may be computed for the ECG cycles relative to the adapted baseline described with reference to 208 of FIG. 2.

Alternatively or additionally, the spatiotemporal variability may be computed for the corrected ECG signals, described with reference to 208 of FIG. 2.

Alternatively or additionally, the spatiotemporal variability may be computed for the coefficients of the regression described with reference to 208 of FIG. 2.

Alternatively or additionally, spatiotemporal variability may be computed for the intervals between an end of an R of a preceding ECG signal and a start of a T of a subsequent ECG signal, as an S-T variability.

Alternatively or additionally, spatiotemporal variability may be computed for the combination further including one or more details of the medical history of the subject.

Alternatively or additionally, spatiotemporal variability of one or more correlations (e.g., computed as described with reference to 208) is computed. When the correlation is computed as a regression (e.g., function), the spatiotemporal variability may be expressed as the coefficients of the regression.

Alternatively or additionally, the spatiotemporal variability of the combination includes variability of voltage of at least the portion of the ECG cycles.

Alternatively or additionally, the spatiotemporal variability of the combination includes variability (e.g., of voltage) of at least a portion of the ECG cycles as a function of the time-synchronized physiological signals. Optionally, the time-synchronized physiological signals comprise respiratory cycles. Each respiratory cycle may include respiratory phases such as an inhalation phase and/or an exhalation phase. The spatiotemporal variability of the combination may include variability of voltage of the ECG cycles as a function of one or more respiratory phases, for example, an inhalation phase and/or an exhalation phase. For subjects with normal responses (e.g., without impact of a heart condition and/or neurological condition on nerve conduction), the rate of the beating heart changes as a function of the respiratory phase (e.g., inhalation and exhalation), i.e., increasing or decreasing as a function of the inhalation and/or exhalation phase. Lack of expected response in changes of the rate of the beating heart with respect to the respiratory phase may indicate the heart condition. For example, when the rate of heartbeats do not slow down and/or speed up as expected for a healthy individual, a likelihood of the heart condition may be determined. Spatiotemporal variability of the combination that is based the ECG in view of the respiratory phase may provide a more accurate indication of the heart condition, in comparison to detecting abnormal response of the heart rate to the inspiration and/or expiration phase alone.

Alternatively or additionally, the spatiotemporal variability of the combination includes variability (e.g., of voltage) of at least the portion of the ECG cycles as a function of variability of blood oxygenation over the cardiac cycles. For subjects with normal responses (e.g., without impact of a heart condition and/or neurological condition on nerve conduction), blood oxygenation may vary as a function of heartbeats. The heart pumping blood into the lungs increases the oxygenation level of the blood, which is then pumped into the rest of the body. A decrease in the oxygenation level of the blood (e.g., partial pressure of oxygen in the blood, such as measured by a pulse oximeter) as a function of the cardiac cycle (e.g., a portion of the ECG cycle) may indicate the heart condition.

Alternatively or additionally, the spatiotemporal variability of the combination includes variability (e.g., of voltage) of the at least the portion of the ECG cycles as a function of variability of blood volume over the cardiac cycles. Changes in blood volume may be measured, for example, using a pulse oximeter. Changes in blood volume may relate to elasticity of the arterial tree, which may be reduced due to stiffness in cardiovascular disease (e.g., due to deposits of plaque). For subjects with normal responses (e.g., without impact of a heart condition and/or neurological condition on nerve conduction), blood volume may vary as a function of heartbeats. The contracting normal heart pushes blood into the vasculature, which results in increased blood volume, especially when the vasculature is healthy and/or elastic. During relaxation, the blood volume may decrease as the blood flows down the vasculature tree, especially when the vasculature is healthy and/or elastic. A change in the dynamics of blood volume as a function of the cardiac cycle (e.g., a portion of the ECG cycle), which may be caused by abnormalities of the beating heart and/or decreased elasticity of the arterial tree, may indicate the heart condition.

Alternatively or additionally, one or more coefficients of a regression between the physiological signal(s) and a target include the ECG cycle(s) corresponding to the physiological signal(s), is computed. The spatiotemporal variability of the combination may include the coefficient(s).

Alternatively or additionally, the spatiotemporal variability of the combination includes variability between successive ECG cycles, for example, variability of a current RR interval with respect to one or more preceding RR intervals.

Available signals may be classified into multiple classification categories. Examples of the available signals include: the ECG signals, the baseline which may be subtracted from the ECG signals, at least one of the time-synchronized physiological signals, delayed version of the physiological signals, and medical data of the subject. Examples of classification categories may include: type of signal, whether the signals are above a median value (e.g., median RR value for the ECG signals) or below the median value, breathing cycle categories such as early exhalation, late exhalation, early inhalation, late inhalation, and the like. The categories may affect the amplitude of at least a portion of the ECG cycle.

The spatiotemporal variability of the combination may be within and/or across the multiple classification categories.

Optionally, one or more correlations within and/or across the classification categories, are computed. The spatiotemporal variability of the combination may include variability of the correlation(s).

Alternatively or additionally, one or more coefficients of a regression between at least one first classification category and a target comprising at least one second classification category, are computed. The spatiotemporal variability of the combination may include the coefficient(s) and/or may include the variability of the coefficient(s).

At 212, the one or more spatiotemporal variabilities of the combination are analyzed.

The analyzing may be performed by extracting one or more features of the one or more spatiotemporal variabilities of the combination, and analyzing the features. Examples of features that may be extracted include: average value of the spatiotemporal variability, spread of the spatiotemporal variability such as maximum value, minimum value, and/or standard deviation, and the like.

The analysis may be performed by feeding the one or more spatiotemporal variabilities and/or the extracted features into a machine learning model. The machine learning model may be trained on a training dataset of records created from data obtained from multiple individuals. A record includes the spatiotemporal variability of the combination and/or features extracted from the spatiotemporal variability, and a ground truth indicating the heart condition of the individual.

An exemplary approach for training the machine learning model is described with reference to FIG. 3.

The analysis may be performed by comparing the one or more spatiotemporal variabilities and/or the extracted features to one or more spatiotemporal variabilities and/or features extracted from other individuals, which do not have the heart condition and which do have the heart condition. For example, a threshold is computed to differentiate between the individual with the heart condition and without the heart condition. The analysis may include comparing the one or more spatiotemporal variabilities and/or the extracted features to the threshold.

At 214, the heart condition may be diagnosed according to the analysis. For example, the heart condition is obtained as an outcome of the machine learning model.

Optionally, the heart condition is coronary artery disease, which is difficult to diagnose non-invasively.

Other examples of heart conditions include: heart failure, arrhythmia, stenotic aortic valve, and the like.

Optionally, an indication of severity of the heart condition is provided according to the analysis.

Optionally, a probability of likelihood of the heart condition is provided according to the analysis.

Optionally, the diagnosis includes a prediction of a future heart condition. For example, prediction of onset of an arrhythmia.

At 216, the subject may be treated according to the diagnosed heart condition. For example, the subject is treated for coronary artery disease of the subject by administering a treatment effective for coronary artery disease. For example, lifestyle changes (e.g., quick smoking, healthy diet, exercise, lose weight), medications (e.g., statins, aspirin, beta-blockers, ace inhibitors, angiotensin II receptor blockers (ARBs), and a medical procedure (e.g., angiography and stent placement, and/or bypass surgery).

Alternatively or additionally, determining likelihood of coronary artery disease by approaches descried herein may be used for improved selection of patents to undergo additional testing, such as invasive testing, for example, angiography.

At 218, one or more features described with reference to 202-216 may be iterated, for example, over multiple time intervals. For example, for monitoring progression and/or regression of the heart condition of the subject over time in response to treatment (e.g., check improvement after the subject takes medications) and/or in response to lack of compliance with treatment by the subject (e.g., subject does not take the prescribed medications).

Referring now back to FIG. 3, at 302, a time-synchronized dataset of an individual subject is created and/or accessed. The time-synchronized dataset includes ECG cycles captured by an ECG sensor over cardiac cycles of the individual that are time-synchronized with physiological signals captured by physiological sensor(s) over physiological cycles of the individual. Additional data such as medical history may be included. Additional exemplary details of the time-synchronized dataset are described, for example, with reference to 202 and/or 204 of FIG. 2.

At 304, pre-processing may be performed. Optionally, a baseline is subtracted from the ECG cycles. Additional exemplary details of pre-processing are described, for example, with reference to 206 of FIG. 2.

At 306, one or more correlations may be computed, for example, as descried with reference to 208 of FIG. 2.

At 308, one or more spatiotemporal variabilities of a combination of at least a portion of the ECG cycles and the time-synchronized physiological signals are computed for example, with reference to 202 and/or 204 of FIG. 2.

At 310, one or more features may be extracted from the spatiotemporal variability, for example, as descried with reference to 212 of FIG. 2.

At 312, an indication of the heart condition of the individual is accessed, for example, automatically extracted from a health record of the individual, manually entered by a user (e.g., via an interface), automatically obtained from medical examinations performed on the individual, and the like.

At 314, a record is created for the individual. The record includes the spatiotemporal variability of the combination and/or features extracted from the spatiotemporal variability, and a ground truth indicating the heart condition of the individual.

At 316, one or more features described with reference to 302 to 314 are iterated, for creating a multi-record training dataset from data of multiple individual.

At 318, a machine learning model is trained on the training dataset. Exemplary machine learning (ML) model architectures include statistical classifiers and/or other statistical models, neural networks of various architectures (e.g., convolutional, fully connected, deep, encoder-decoder, recurrent, transformer, graph), support vector machines (SVM), logistic regression, k-nearest neighbor, decision trees, boosting, random forest, a regressor, and/or any other commercial or open source package allowing regression, classification, dimensional reduction, supervised, unsupervised, semi-supervised, and/or reinforcement learning. Machine learning models may be trained using supervised approaches and/or unsupervised approaches.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant sensors will be developed and the scope of the term sensor is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A coronary artery disease treatment method, comprising:

collecting from a subject, a time-synchronized dataset including a plurality of ECG cycles captured by an ECG sensor over a plurality of cardiac cycles that are time-synchronized with a plurality of physiological signals captured by at least one physiological sensor over a plurality of physiological cycles of the subject;

identifying the subject with coronary artery disease based on:

subtracting a baseline from the plurality of ECG cycles;

computing spatiotemporal variability of a combination of at least a portion of the plurality of ECG cycles and the time-synchronized plurality of physiological signals, wherein the spatiotemporal variability of the combination includes variability of at least a portion of the plurality of ECG cycles as a function of the time-synchronized physiological signals;

analyzing the spatiotemporal variability of the combination including the variability of the at least the portion of the plurality of ECG cycles as the function of the time-synchronized physiological signals; and administering an appropriate treatment to the subject with coronary artery disease, wherein the appropriate treatment is selected from: quitting smoking, healthy diet, exercise, losing weight, statins, aspirin, beta-blockers, ace inhibitors, angiotensin II receptor blockers (ARBs), and angiography with stent placement, bypass surgery, and combinations of the aforementioned.

2. The method of claim 1, further comprising:

for each ECG cycle of the plurality of ECG cycles, computing at least one correlation between at least one of:

(i) the at least the portion of the ECG cycle and at least one corresponding individual physiological signal;

(ii) the at least the portion of the ECG cycle and at least one other portion of the ECG cycle;

(iii) the at least the portion of the respective individual ECG cycles and medical history of the subject;

wherein computing the spatiotemporal variability of the combination comprises computing spatiotemporal variability of the at least one correlation over the plurality of ECG cycles.

3. The method of claim 2, wherein the correlation comprises a regression, and the spatiotemporal variability is expressed as the coefficients of the regression.

4. The method of claim 2, further comprising computing an adapted baseline by adapting the baseline according to the correlation, wherein the spatiotemporal variability is computed for the plurality of ECG cycles relative to the adapted baseline.

5. The method of claim 1, further comprising accessing medical records including the medical history of the subject, and wherein the spatiotemporal variability of the combination is analyzed with the medical history.

6. The method of claim 1, further comprising extracting at least one feature of the spatiotemporal variability of the combination, wherein analyzing comprises feeding the at least one feature into a machine learning model, and wherein the diagnosis of the heart condition is obtained as an outcome of the machine learning model.

7. The method of claim 6, wherein the machine learning model is trained on a training dataset of a plurality of records for a plurality of individuals, wherein a record includes the at least one feature of spatiotemporal variability of the combination extracted from the time-synchronized dataset of an individual, and a ground truth indicating the heart condition of the individual.

8. The method of claim 1, wherein the spatiotemporal variability of the combination comprises variability of voltage of at least the portion of the plurality of ECG cycles.

9. The method of claim 1, wherein the spatiotemporal variability of the combination comprises variability of voltage of the plurality of ECG cycles as a function of the time-synchronized plurality of physiological signals.

10. The method of claim 1, wherein the plurality of physiological signals captured by at least one physiological sensor over a plurality of physiological cycles of the subject include a plurality of breathing signals captured by at least one respiration sensor over a plurality of respiratory cycles.

11. The method of claim 10, wherein the spatiotemporal variability of the combination comprises variability of voltage of the plurality of ECG cycles as a function of the plurality of respiratory cycles.

12. The method of claim 11, wherein the spatiotemporal variability of the combination comprises variability of voltage of at least a portion of the ECG cycles as a function of an inhalation phase and/or an exhalation phase.

13. The method of claim 10, wherein the plurality of breathing signals are captured by at least one respiration sensor comprising a tension sensor indicating changes in tension of a belt placed around a chest of the subject in response to expansion and contraction of the chest during inhalation and exhalation.

14. The method of claim 1, wherein the plurality of physiological signals captured by at least one physiological sensor over a plurality of physiological cycles of the subject include blood oxygenation signals captured by at least one blood oxygenation sensor over the plurality of cardiac cycles.

15. The method of claim 14, wherein the spatiotemporal variability of the combination comprises variability of voltage of at least a portion of the ECG cycles as a function of variability of blood oxygenation over the cardiac cycles.

16. The method of claim 1, wherein the plurality of physiological signals captured by at least one physiological sensor over a plurality of physiological cycles of the subject include blood volume signals denoting changes in blood volume captured by at least one blood volume sensor over the plurality of cardiac cycles.

17. The method of claim 16, wherein the spatiotemporal variability of the combination comprises variability of voltage of the plurality of ECG cycles as a function of variability of blood volume over the cardiac cycles.

18. The method of claim 1, wherein the at least the portion of the plurality of ECG cycles is selected from: between P and Q, between Q and R, between R and S, between S and T.

19. The method of claim 1, further comprising:

computing a delay between the physiological signals, and each one of a preceding corresponding ECG cycle; and time shifting the plurality of physiological signals to correspond to the plurality of ECG cycles;

wherein the spatiotemporal variability is computed between the plurality of ECG cycles and the time shifted plurality of physiological signals.

20. The method of claim 1, wherein the spatiotemporal variability of the combination includes variability between successive ECG cycles.

21. The method of claim 1, further comprising:

classifying available signals into a plurality of classification categories;

wherein computing the spatiotemporal variability of the combination comprises computing spatiotemporal variability within and/or across the plurality of classification categories.

22. The method of claim 1, further comprising:

classifying available signals into a plurality of classification categories;

wherein computing the spatiotemporal variability of the combination comprises computing at least one correlation within and/or across the plurality of classification categories, wherein the spatiotemporal variability is of the at least one correlation.

23. The method of claim 1, further comprising:

classifying available signals into a plurality of classification categories;

wherein computing the spatiotemporal variability of the combination comprises at least computing at least one coefficient of a regression between at least one first classification category and a target comprising at least one second classification category, wherein the spatiotemporal variability of the combination includes the at least one coefficient and/or is of the at least one coefficient.

24. The method of claim 21, wherein available signals include one or more of:

(i) plurality of ECG signals, (ii) the baseline subtracted from the plurality of ECG signals, (iii) at least one of the time-synchronized plurality of physiological signals, (iv) delayed version of the plurality of physiological signals, (v) medical data of the subject.

25. The method of claim 21, wherein the plurality of classification categories include a first classification category indicating that a time interval of an ECG signal is above a median of time intervals of the plurality of ECG signals, and a second classification category indicating that the time interval of the ECG signal is below the median.

26. The method of claim 1, further comprising:

computing at least one coefficient of a regression between the plurality of physiological signal and a target comprising an ECG cycle of the plurality of ECG cycles corresponding to a physiological signal of the plurality of physiological signals;

wherein the spatiotemporal variability of the combination includes the at least one coefficient.

27. The method of claim 1, further comprising:

computing a correlation between the plurality of ECG cycles and the plurality of physiological signals;

computing an initial baseline according to a common portion of the plurality of ECG cycles of a raw ECG signal;

adapting the initial baseline according to the correlation to compute an adapted baseline;

adjusting the raw ECG signal according to the adapted baseline to obtain a corrected ECG signal, wherein the spatiotemporal variability is computed for the correct ECG signal.

28. A method of training a machine learning model for diagnosis a heart condition of a subject, comprising:

creating a multi-record training dataset for a plurality of individual, wherein a record comprises:

at least one feature of spatiotemporal variability of a combination extracted from a time-synchronized data-set, and a ground truth indicating the heart condition of the individual, wherein the heart condition comprises coronary artery disease wherein the at least one feature is computed by:

accessing the time-synchronized dataset including a plurality of ECG cycles captured by an ECG sensor over a plurality of cardiac cycles of the individual that are time-synchronized with a plurality of physiological signals captured by at least one physiological sensor over a plurality of physiological cycles of the individual;

subtracting a baseline from the plurality of ECG cycles;

computing the at least one feature as a spatiotemporal variability of a combination of at least a portion of the ECG cycles and the time-synchronized plurality of physiological signals, wherein the spatiotemporal variability of the combination includes variability of at least a portion of the plurality of ECG cycles as a function of the time-synchronized physiological signals;

training the ML model on the multi-record training dataset;

diagnosing the subject with coronary artery disease using the ML model trained on the multi-record training dataset; and treating the coronary artery disease of the subject by administering a treatment effective for coronary artery disease selected from: quitting smoking, healthy diet, exercise, losing weight, statins, aspirin, beta-blockers, ace inhibitors, angiotensin II receptor blockers (ARBs), and angiography with stent placement, bypass surgery, and combinations of the aforementioned.

29. A device for diagnosing a coronary artery disease in a subject, comprising:

an ECG interface for connecting to at least one ECG sensor;

at least one second interface for connecting to at least one physiological sensor;

circuitry configured for generating a time-synchronized dataset including a plurality of ECG cycles captured by the ECG sensor over a plurality of cardiac cycles of the subject that are time-synchronized with a plurality of physiological signals captured by the at least one physiological sensor over a plurality of physiological cycles of the subject; and at least one processing executing a code for:

subtracting a baseline from the plurality of ECG cycles;

computing spatiotemporal variability of a combination of at least a portion of the plurality of ECG cycles and the time-synchronized plurality of physiological signals, wherein the spatiotemporal variability of the combination includes variability of at least a portion of the plurality of ECG cycles as a function of the time-synchronized physiological signals;

analyzing the spatiotemporal variability of the combination including the variability of the at least the portion of the plurality of ECG cycles as the function of the time-synchronized physiological signals;

diagnosing coronary artery disease according to the analysis;

and treating the coronary artery disease of the subject by administering a treatment effective for coronary artery disease selected from: quitting smoking, healthy diet, exercise, losing weight, statins, aspirin, beta-blockers, ace inhibitors, angiotensin II receptor blockers (ARBs), and angiography with stent placement, bypass surgery, and combinations of the aforementioned.

* * * * *